United States Patent
Aujla

(10) Patent No.: US 12,390,141 B2
(45) Date of Patent: Aug. 19, 2025

(54) CATHETER WITH BIPOLE ELECTRODE SPACER AND RELATED METHODS

(71) Applicant: Biosense Webster (Israel) Ltd., Yokneam (IL)

(72) Inventor: Vishav Manak Singh Aujla, Valencia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 895 days.

(21) Appl. No.: 17/228,571

(22) Filed: Apr. 12, 2021

(65) Prior Publication Data

US 2021/0228137 A1 Jul. 29, 2021

Related U.S. Application Data

(63) Continuation of application No. 16/920,335, filed on Jul. 2, 2020, now Pat. No. 10,973,427, which is a
(Continued)

(51) Int. Cl.
*A61B 18/14* (2006.01)
*A61B 5/00* (2006.01)
(Continued)

(52) U.S. Cl.
CPC ............ *A61B 5/287* (2021.01); *A61B 5/0036* (2018.08); *A61B 5/4836* (2013.01);
(Continued)

(58) Field of Classification Search
CPC ..... A61B 5/287; A61B 5/0036; A61B 5/4836; A61B 5/6858; A61B 5/6859;
(Continued)

(56) References Cited

U.S. PATENT DOCUMENTS 6,961,602 B2 11/2005 Fuimaono et al.
8,287,532 B2 10/2012 Carroll et al.
(Continued)

FOREIGN PATENT DOCUMENTS

CN 102895027 A 1/2013
CN 103547213 A 1/2014
(Continued)

OTHER PUBLICATIONS

European Patent Office Search Report for EP Application No. 17187677.4 dated Jan. 19, 2018, 13 pages.
(Continued)

*Primary Examiner* — Adam Z Minchella
(74) *Attorney, Agent, or Firm* — FROST BROWN TODD LLP

(57) ABSTRACT

An electrophysiology catheter constructed with assembly and wiring of ring electrodes using spacer rings of electrically-nonconductive material, whose length is predetermined/premeasured, includes a distal section with at least one spine having two electrodes, and a spacer member therebetween, wherein the spacer member configured to provide a separation gap between the two electrodes. The separation gap may span in an axial direction and/or in a circumferential direction. The spacer member may be configured generally as a ring with a center axial opening configured to receive the spine therethrough. The spacer member may include an axial extension providing a first separation gap between a first pair of electrodes in a circumferential direction, and a circumferential providing a second separation gap between a second pair of electrodes in an axial direction

20 Claims, 8 Drawing Sheets

Related U.S. Application Data continuation of application No. 15/246,450, filed on Aug. 24, 2016, now Pat. No. 10,702,177.

(51) Int. Cl.
| | | |
|---|---|---|
| *A61B 5/287* | (2021.01) | |
| *A61M 25/00* | (2006.01) | |
| *A61B 17/00* | (2006.01) | |
| *A61B 18/00* | (2006.01) | |

(52) U.S. Cl.
CPC .......... *A61B 5/6858* (2013.01); *A61B 5/6859* (2013.01); *A61B 18/1492* (2013.01); *A61M 25/0082* (2013.01); *A61B 2017/00526* (2013.01); *A61B 2018/00083* (2013.01); *A61B 2018/0016* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2018/1467* (2013.01); *A61M 2025/0096* (2013.01)

(58) Field of Classification Search
CPC ...... A61B 18/1492; A61B 2017/00526; A61B 2018/00083; A61B 2018/0016; A61B 2018/00267; A61B 2018/00351; A61B 2018/00357; A61B 2018/00577; A61B 2018/00839; A61B 2018/1467; A61M 25/0082; A61M 2025/0096

See application file for complete search history.

(56) References Cited

U.S. PATENT DOCUMENTS

| | | | |
|---|---|---|---|
| 9,907,480 B2 | 3/2018 | Basu et al. | |
| 10,702,177 B2 | 7/2020 | Aujla | |
| 10,973,427 B2 | 4/2021 | Aujla | |
| 2001/0025177 A1* | 9/2001 | Woloszko | A61B 18/1492 606/41 |
| 2001/0031942 A1* | 10/2001 | Tollner | A61B 18/1492 606/47 |
| 2002/0013537 A1 | 1/2002 | Rock | |
| 2003/0125614 A1* | 7/2003 | Fuimaono | A61B 5/287 600/374 |
| 2005/0075554 A1 | 4/2005 | Bernhart et al. | |
| 2007/0219551 A1 | 9/2007 | Honour et al. | |
| 2011/0047795 A1 | 3/2011 | Turner et al. | |
| 2011/0130817 A1 | 6/2011 | Chen | |
| 2012/0179018 A1 | 7/2012 | Rock | |
| 2012/0203320 A1 | 8/2012 | Digiore et al. | |
| 2014/0025072 A1 | 1/2014 | Mirizzi et al. | |
| 2014/0228838 A1 | 8/2014 | Kirschenman | |
| 2015/0351652 A1* | 12/2015 | Marecki | A61B 18/1492 29/829 |

FOREIGN PATENT DOCUMENTS

| | | |
|---|---|---|
| CN | 104519786 A | 4/2015 |
| CN | 104684499 A | 6/2015 |
| CN | 104837430 A | 8/2015 |
| CN | 104968261 A | 10/2015 |
| CN | 105263568 A | 1/2016 |
| CN | 105615994 A | 6/2016 |
| EP | 3040043 A1 | 7/2016 |
| JP | H10-509338 A | 9/1998 |
| WO | WO 2014/124231 A1 | 8/2014 |
| WO | WO 2016/130713 A1 | 8/2016 |
| WO | WO 2017/048965 | 3/2017 |

OTHER PUBLICATIONS

Chinese First Office Action and Search Report dated Jul. 6, 2021, for Application No. 201710735843.X, 9 pages.
Chinese First Office Action and Search Report dated May 23, 2023, for Application No. 202210103732.8, 7 pages.
Chinese Second Office Action and Search Report dated Oct. 26, 2023, for Application No. 202210103732.8, 10 pages.
European Communication dated Jun. 1, 2021, for Application No. 17187677.4, 10 pages.
Japanese First Office Action dated Aug. 31, 2021, for Application No. 2017-160034, 7 pages.
Japanese Final Office Action dated May 31, 2022, for Application No. 2017-160034, 3 pages.

* cited by examiner

CATHETER WITH BIPOLE ELECTRODE SPACER AND RELATED METHODS

CROSS-REFERENCE TO RELATED APPLICATION(S)

This application is a continuation of and claims priority to and the benefit of U.S. patent application Ser. No. 16/920,335, filed Jul. 2, 2020, now U.S. Pat. No. 10,973,427, which is a continuation of and claims priority to and the benefit of U.S. patent application Ser. No. 15/246,450 filed Aug. 24, 2016, now U.S. Pat. No. 10,702,177, the entire contents of all of which are incorporated herein by reference.

FIELD OF INVENTION

This invention relates to an electrophysiology catheter, in particular, a cardiac electrophysiology catheter with an electrode configuration that provides for more accurate and discrete sensing.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiology mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with the endocardium. By monitoring the electrical signals at the endocardium, aberrant conductive tissue sites responsible for the arrhythmia can be pinpointed.

For sensing by ring electrodes mounted on a catheter, lead wires transmitting signals from the ring electrodes are electrically connected to a suitable connector in the distal end of the catheter control handle, which is electrically connected to an ECG monitoring system and/or a suitable 3-D electrophysiology (EP) mapping system, for example, CARTO, CARTO XP or CARTO 3, available from Biosense Webster, Inc. of Irwindale, California.

Regardless of the size and number of the ring electrodes, ring electrode pairs are evenly spaced along the catheter. The closely-spaced electrode pairs allow for more accurate detection of near-field potentials versus far-field signals, which can be very important when trying to treat specific areas of the heart. For example, near-field pulmonary vein potentials are smaller/weaker signals whereas the atria, located very close to the pulmonary vein, provides much larger/stronger signals. Accordingly, even when the catheter is placed in the region of a pulmonary vein, it can be difficult for the electrophysiologist to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

However, manufacturing and assembling catheters with closely and precisely spaced ring electrodes pose many challenges. Where desired spacing between electrode pairs range on the order of millimeters or even microns, accuracy and consistency in spacing become critical to catheter manufacturing and assembly. Conventional methods often use adhesives such as polyurethane to seal each ring electrode, which creates a margin between adjacent electrode or electrode pairs that limits how closely the electrodes can be spaced from each other. Spacing of 1.0 mm or larger between electrode pairs can be achieved using such conventional methods. However, spacing smaller, especially 0.2 or 0.1 mm spacing is difficult to achieve. At such smaller spacing, there is the risk of two electrodes in contact due to electrode tolerance specification or shifting of electrodes during assembly when medical grade adhesive such as Polyurethane is applied or when medical epoxy is curing.

Moreover, the conventional methods of attaching a lead wire to a ring electrode also typically require spacing tolerances between adjacent ring electrodes. Such attachment methods often result in an acute angle at which the lead wire must extend to reach the ring electrode which can stress the lead wire and result in detachment or breakage.

Accordingly, a need exists for an electrophysiology catheter with a ring electrode configuration that provides very closely spaced electrodes with minimized stress and strain to attached lead wires. There is also a need for a method of manufacture and assembly of such a catheter wherein very close spacing between electrodes can be achieved readily and consistently with improved precision and accuracy.

SUMMARY OF THE INVENTION

The present invention is directed to an electrophysiology catheter with electrodes having predetermined spacing. The catheter construction simplifies the assembly and wiring of the ring electrodes by employing spacer rings made of a biocompatible, electrically-nonconductive material, whose length is predetermined/premeasured so that manufacturing and assembly processes are simplified with improved accuracy and consistency.

In some embodiments, an electrophysiology catheter of the present invention comprises an elongated body, and a distal section distal of the elongated body, the distal section including one spine having two electrodes, and a spacer member having at least a portion spanning between the two electrodes, wherein the spacer member is made of a nonconductive material and the portion is configured to provide a separation gap between the two electrodes. In some embodiments, the separation gap spans in an axial direction. In some embodiments, the separation gap spans in a circumferential direction.

In some embodiments, the spacer member is configured generally as a ring with a center axial opening configured to receive the spine therethrough.

In some embodiments, the spacer member is configured with a distal edge and a proximal edge, the distal edge configured to abut with a proximal end of a distal ring electrode and the proximal edge configured to abut with a distal end of a proximal ring electrode.

In some embodiments, the spacer member includes an axial extension configured to provide a first separation gap between a first pair of electrodes in a circumferential direction and a circumferential extension configured to provide a second separation gap between a second pair of electrodes in an axial direction.

In some embodiments, the spacer member includes an axial extension spanning between a first pair of electrodes in the circumferential direction, and a circumferential extension spanning between a second pair of electrodes.

In some embodiments, the spacer member has first and second axial extensions, and at least one circumferential extension extending between the first and second axial extensions.

In some embodiments, an electrophysiology catheter of the present invention comprises an elongated body, and a distal electrode assembly having a plurality of spines, a spine having a plurality of electrodes and a spacer member therebetween, the spacer member being made of a nonconductive material and configured with an axial through-hole, the spacer member being configured with recessed voids occupied by the electrodes in providing an axial separation gap between a first pair of adjacent electrodes and a circumferential separation gap between a second pair of adjacent electrodes.

In some embodiments, the spacer member has a generally hollow cylindrical configuration, a first circumferential extension and a first axial extension.

In some embodiments, the first circumferential extension extends between the first axial extension and a second axial extension.

In some embodiments, the first circumferential extension and the first and second axial extension define a recessed void in the spacer member.

In some embodiments, for an electrophysiology catheter having an elongated body, and a distal electrode assembly having a plurality of spines, a spine having a plurality of electrodes and a spacer member therebetween, the spacer member being made of a nonconductive material and configured with an axial through-hole, the spacer member being configured with recessed voids occupied by the electrodes in providing an axial separation gap between a first pair of adjacent electrodes and a circumferential separation gap between a second pair of adjacent electrodes, a method comprising includes inserting a distal end of the spine through the axial through-hole of the spacer member, sliding the spacer member along the spine to a predetermined position on the spine, and positioning each electrode in a respective recessed void.

In some embodiments, for an electrophysiology catheter having an elongated body, and a distal section distal of the elongated body, the distal section including one spine having two electrodes, and a spacer member having at least a portion spanning a predetermined distance between the two electrodes, wherein the spacer member is made of a nonconductive material and the spacer member having at least two recessed voids, and a respective lead wire for each electrode, a method of assembling comprises connecting a distal end of each lead wire to a respective ring electrode, sliding a first ring electrode on the spine, sliding the spacer member on the spine, sliding a second ring electrode on the spine, and abutting the first and second ring electrodes against the spacer member.

In some embodiments, the method further comprises connecting a distal end of each lead wire to a respective electrode, sliding the spacer member onto the spine, and positioning each electrode in a respective void of the spacer member.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
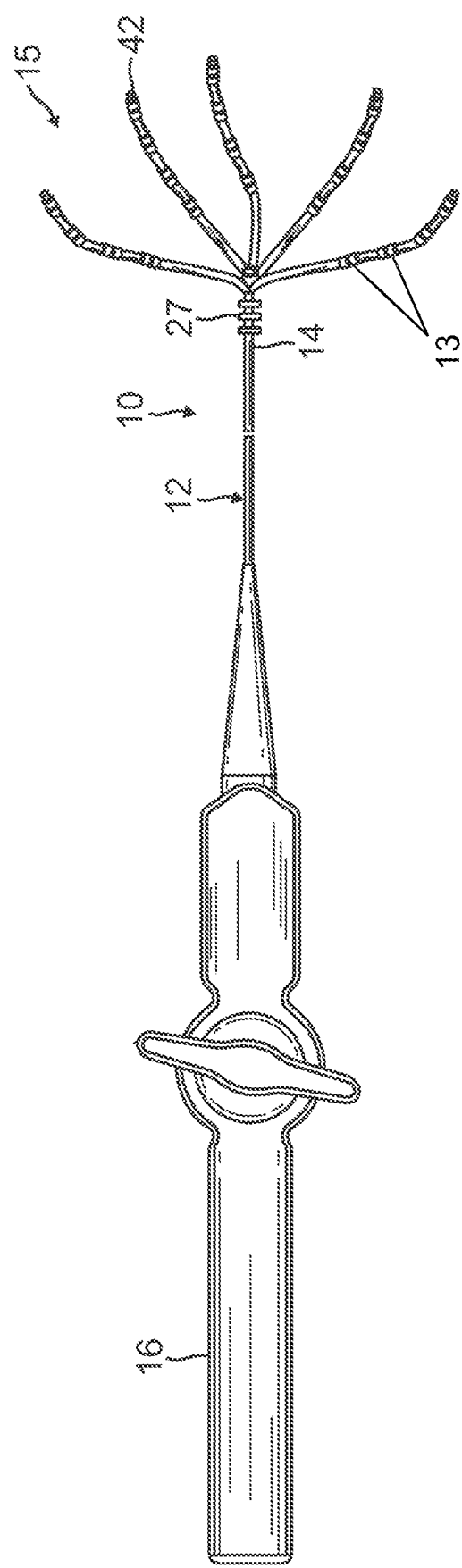
FIG. 1 is a side view of a catheter of the present invention, in accordance with an embodiment.

Referring to FIG. 1, in some embodiment of present invention, a catheter 10 includes a catheter body 12, an intermediate deflection section 14, a distal electrode assembly 15, and a control handle 16 proximal of the catheter body 12. The distal electrode assembly 15 includes a plurality of spines 42, each spine carrying at least one pair of closely-spaced electrodes 13, wherein the electrodes of a pair has a spacer defining a separation space gap distance ranging between about 50 microns and 200 microns, and preferably between about 50 and 100 microns.

Figure 2:
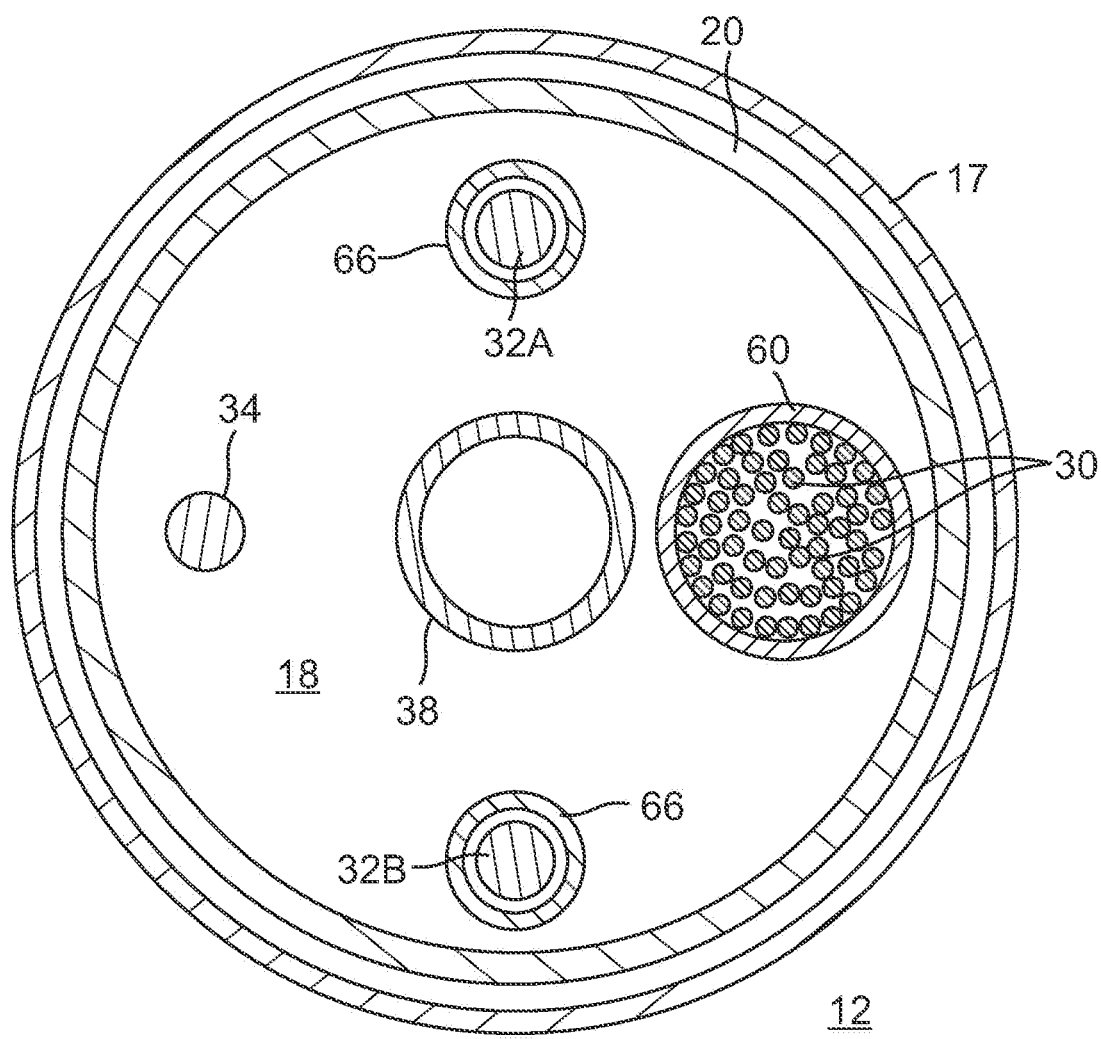
FIG. 2 is an end cross-sectional view of a catheter body of the catheter of FIG. 1.

In some embodiments, the catheter body 12 comprises an elongated tubular construction, having a single, axial or central lumen 18, as shown in FIG. 2. The catheter body 12 is flexible, i.e., bendable, but substantially non-compressible along its length. The catheter body 12 can be of any suitable construction and made of any suitable material. A presently preferred construction comprises an outer wall 17 made of a polyurethane, or PEBAX. The outer wall 17 comprises an imbedded braided mesh of high-strength steel, stainless steel or the like to increase torsional stiffness of the catheter body 12 so that, when the control handle 16 is rotated, the deflection section 14 of the catheter 10 will rotate in a corresponding manner.

The outer diameter of the catheter body 12 is not critical, but is preferably no more than about 8 french, more preferably about 7 french. Likewise the thickness of the outer wall 17 is not critical, but is thin enough so that the central lumen 18 can accommodate components, including, for example, one or more puller wires, electrode lead wires, irrigation tubing, and any other wires and/or cables. The inner surface of the outer wall 17 is lined with a stiffening tube 20, which can be made of any suitable material, such as polyimide or nylon. The stiffening tube 20, along with the braided outer wall 17, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 17. In some embodiments, polyimide tubing is used for the stiffening tube 20 because it may be very thin walled while still providing very good stiffness. This maximizes the diameter of the central lumen 18 without sacrificing strength and stiffness. As would be recognized by one skilled in the art, the catheter body construction can be modified as desired. For example, the stiffening tube can be eliminated.

Figure 3:
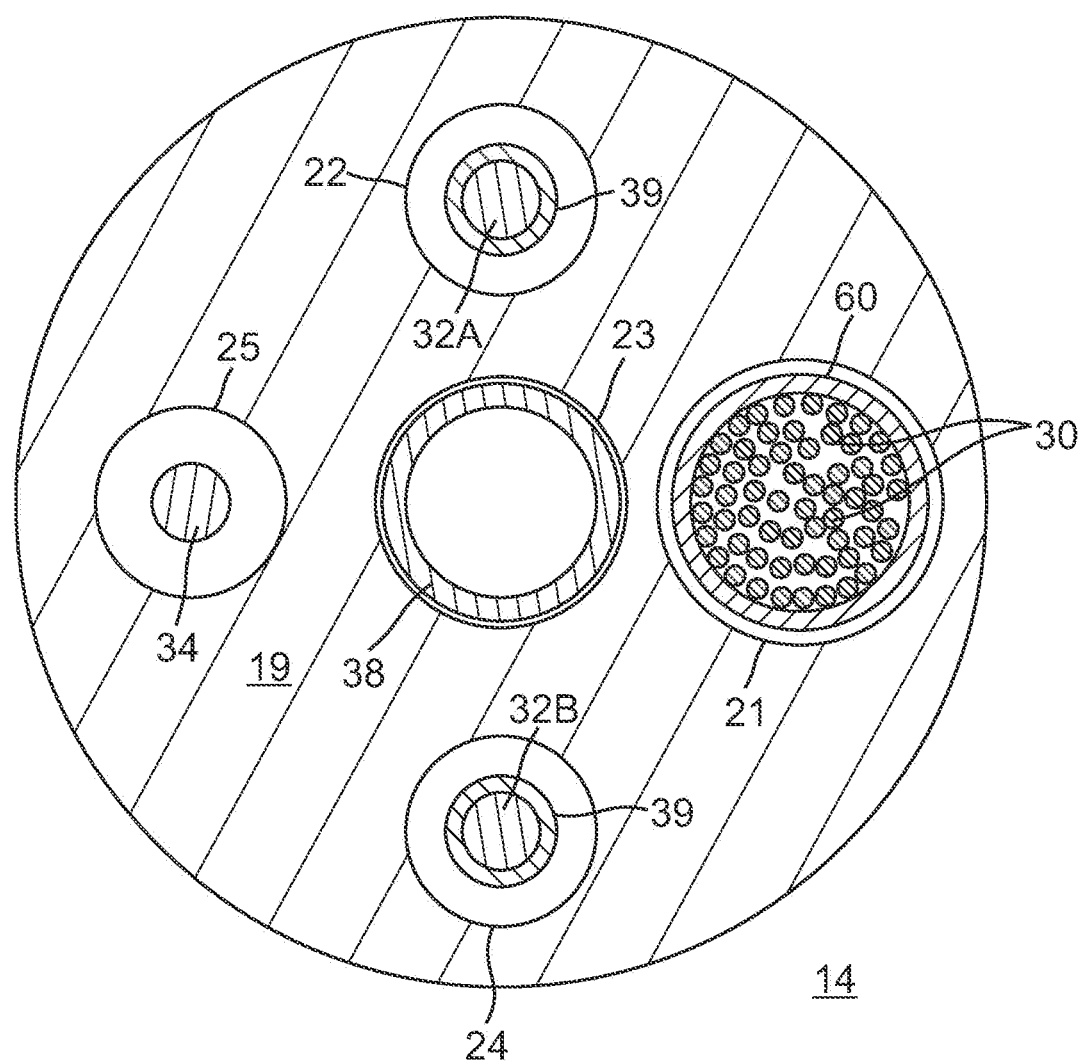
FIG. 3 is an end cross-sectional view of an intermediate deflection section of the catheter of FIG. 1.

In some embodiments, the intermediate deflection section comprises a shorter section of tubing 19, which as shown in FIG. 3, has multiple lumens, for example, off-axis lumens 21, 22, and 25 24 and on-axis lumen 23. In some embodiments, the tubing 19 is made of a suitable non-toxic material more flexible than the catheter body 12. A suitable material for the tubing 19 is braided polyurethane, i.e., polyurethane with an embedded mesh of braided high-strength steel, stainless steel or the like. The outer diameter of the deflection section 14 is similar to that of the catheter body 12. The size of the lumens is not critical and can vary depending on the specific application.

Figure 4:
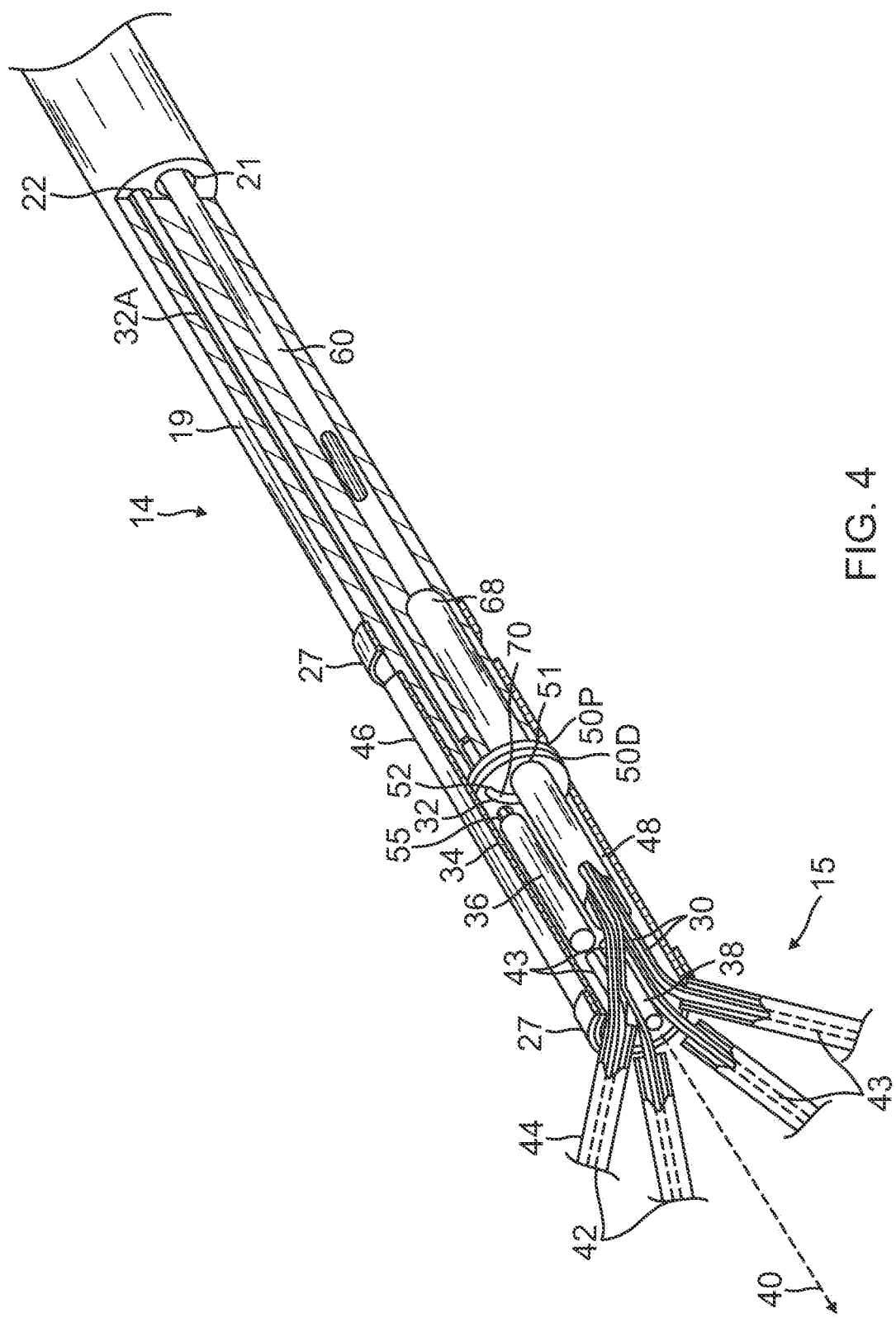
FIG. 4 is a perspective view of a junction between the intermediate deflection section and a distal electrode assembly of the catheter of FIG. 1.

Various components extend through the catheter 10. In some embodiments, the components include lead wires 30 for electrodes on the distal electrode assembly 15, one or more puller wires 32A and 32B for deflecting the deflection section 14, a cable 34 for an electromagnetic position sensor 36 housed at or near a distal end of the deflection section 14, and a guidewire tubing 38, as shown in FIG. 4. These components pass through the central lumen 18 of the catheter body 12, as shown in FIG. 2.

In the deflection section 14, different components pass through different lumens of the tubing 19 as shown in FIG. 3. In some embodiments, the lead wires 30 pass through first lumen 21, the first puller wire 32A passes through second lumen 32, the guidewire tubing 38 passes through third lumen 23, the cable 34 passes through fourth lumen 24, and the second puller 34B passes through fifth lumen 25. The second and fourth lumens 22 and 24 are diametrically opposite of each other to provide bi-directional deflection of the intermediate deflection section 14.

With reference to FIG. 4, distal of the deflection section 14 is the distal electrode assembly 15 which includes a mounting stem 46 in the form of a shorter tubing mounted on a distal end of the tubing 19 of the intermediate deflection section 14. (In that regard, it is understood that where the catheter 10 is without a deflection section 14, the mounting stem 46 is mounted on a distal end of the catheter body 12.) The stem 46 has a central lumen 48 to house various components. The intermediate section 14 and stem 46 are attached by glue or the like. The stem 46 may be constructed of any suitable material, including nitinol. The stem 46 houses various components, including the electromagnetic position sensor 36, and a distal anchor for the puller wires 32A and 32B.

In the disclosed embodiment, the distal anchor includes one or more washers, for example, a distal washer 50D and a proximal washer 50P, each of which has a plurality of through-holes that allow passage of components between the deflection section 14 and the stem 46 while maintaining axial alignment of these components relative to a longitudinal axis 40 of the catheter 10. The through-holes include holes 52 and 54 that are axially aligned with the second and fourth lumens 22 and 24 of the tubing 19, respectively, to receive a distal end of puller wires 32A and 32B, respectively. It is understood that the puller wires 32A and 32B may be formed as a single tensile member 32 with a distal U-bend section 70 that passes through the holes 52 and 54, as shown in FIG. 4. With tension on the washers 50D and 50P exerted by the U-bend section of the puller wires, the washers firmly and fixedly abut against the distal end of the tubing 19 of the deflection section 14 to distally anchor the U-bend section.

Each washer includes through-hole 51 which is axially aligned with the first lumen 21 and allows passage of the lead wires 30 from the deflection section 14 and into the lumen 48 of the stem 46. Each washer also includes through-hole 55 which is axially aligned with the fifth lumen 25 of the tubing 19 and allows passage of the sensor cable 34 from the deflection section 14 into lumen 48 of the stem 46 where the electromagnetic position sensor 36 is housed. Each washer further includes on-axis through-hole 53 which is axially aligned with the third lumen 23 and allows passage of the guidewire tubing 38 from the deflection section 14 into the lumen 48 of the stem 46. Marker bands or ring electrodes 27 may be carried on the outer surface of the catheter at or near the near the distal end of the intermediate deflection section 14, as known in the art.

Each puller wire 32A and 32B is anchored at its proximal end in the control handle 16 (FIG. 1). In some embodiments, the puller wires have at least sections made of any suitable metal, such as stainless steel or Nitinol, and are preferably coated with Teflon® or the like. The coating imparts lubricity to the puller wires.

A compression coil 66 is situated within the catheter body 12 in surrounding relation to each puller wire, as shown in FIG. 2. The compression coils 66 extend from the proximal end of the catheter body 12 to about the proximal end of the deflection section 14. The compression coils are made of any suitable metal, preferably stainless steel. Each compression coil is tightly wound on itself to provide flexibility, i.e., bending, but to resist compression. The inner diameter of the compression coil is preferably slightly larger than the diameter of the puller wire. The Teflon® coating on the puller wire allows it to slide freely within the compression coil. The puller wire 32A extends through the lumen 22 of the tubing 19 and the puller wire 32B extends through the lumen 24 of the tubing 19. Within these lumens, each puller wire extends through a respective plastic, preferably Teflon®, sheath 39 (see FIG. 3), which prevents the puller wires from cutting into the wall of the tubing 19 when the deflection section 14 is deflected.

Longitudinal movement of the puller wires relative to the catheter body 12, which results in deflection of the tip section 14, is accomplished by suitable manipulation of the control handle 16. A suitable control handle design for use with the present invention is described in U.S. Pat. No. 8,287,532, the entire disclosure of which is incorporated herein by reference. If desired, the catheter can be uni-deflectional, i.e., having only one puller wire.

As shown in FIG. 4, extending from the distal end of the stem 46 are elongated spines 42 of the distal electrode assembly 15. Each spine has a support member 43 and a non-conductive covering 44 that extends along the each spine 42. Each spine has a proximal portion that extends proximally into the lumen 48 of the stem 46. The nonconductive coverings 44 of the spines may also extend proximally into the lumen 48. Each spine 42 may be arranged uniformly about the distal opening of the stem 46 in equi-radial distance from adjacent spines 42. For example, with five spines, each spine may be spaced apart at about 72 degrees from adjacent spines. Suitable adhesive, e.g., polyurethane, may be used to pot and anchor the proximal ends of the spines 42 and their nonconductive coverings 44. The suitable adhesive seals the distal end of the stem 46, which is formed to leave open the distal end of the guidewire tubing 38.

Each spine support member 43 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 44 can be made of any suitable material, and is preferably made of a biocompatible plastic such as polyurethane or PEBAX.

Lead wires 30 for microelectrodes carried on the spines 42 extend through the catheter body 12 and the deflection section 14 protected by a nonconductive sheath 60. Toward the distal electrode assembly 15, the lead wires 30 extend through a polytube 68, as shown in FIG. 4. The lead wires 30 diverge at the distal end of the polytube 68, and extend toward their respective spine support member 43, into their respective nonconductive covering 44 of their respective spine 42.

Figure 5:
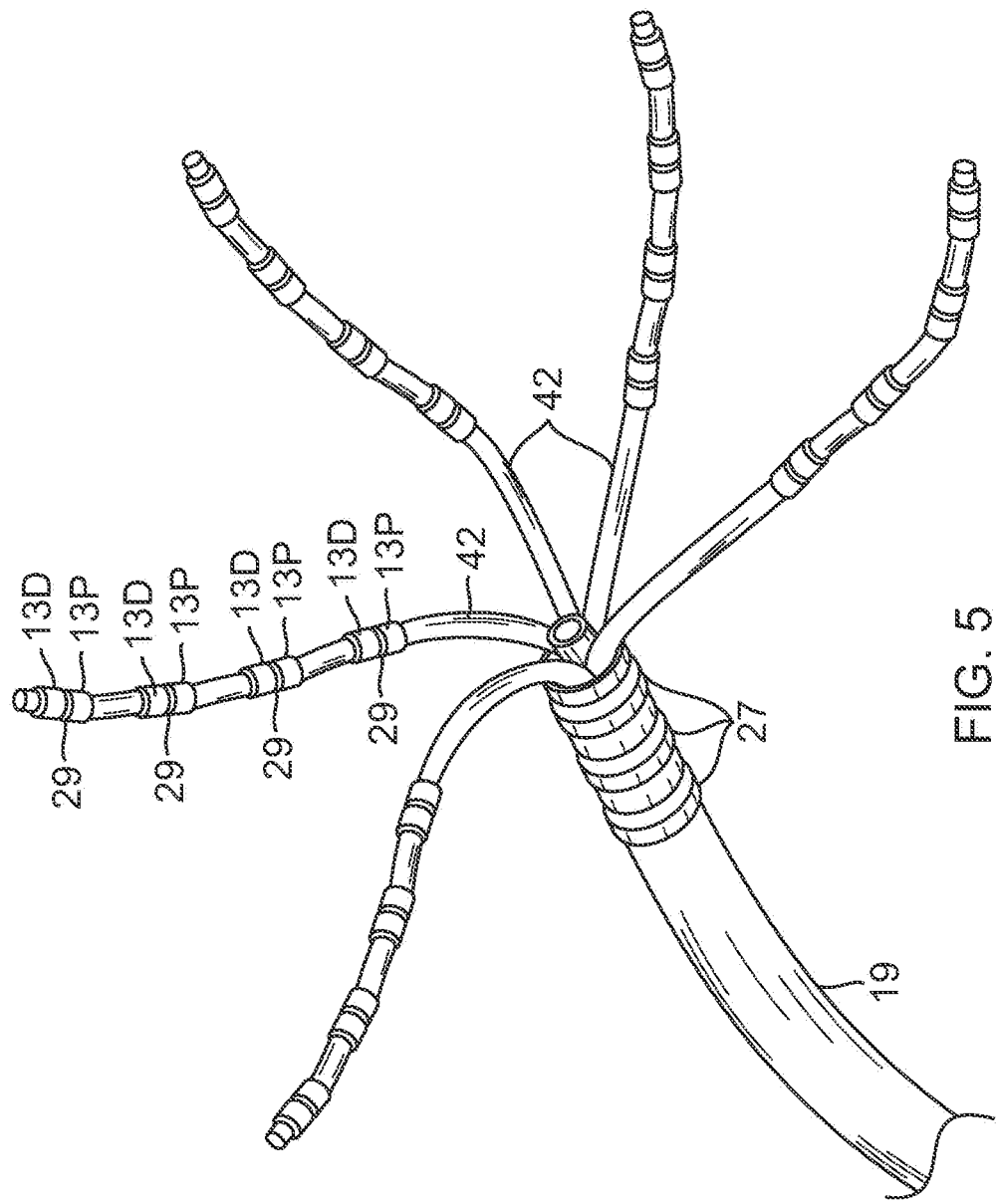
FIG. 5 is a perspective view of a distal electrode assembly of the present invention, in accordance with an embodiment.
Figures 6, 7:
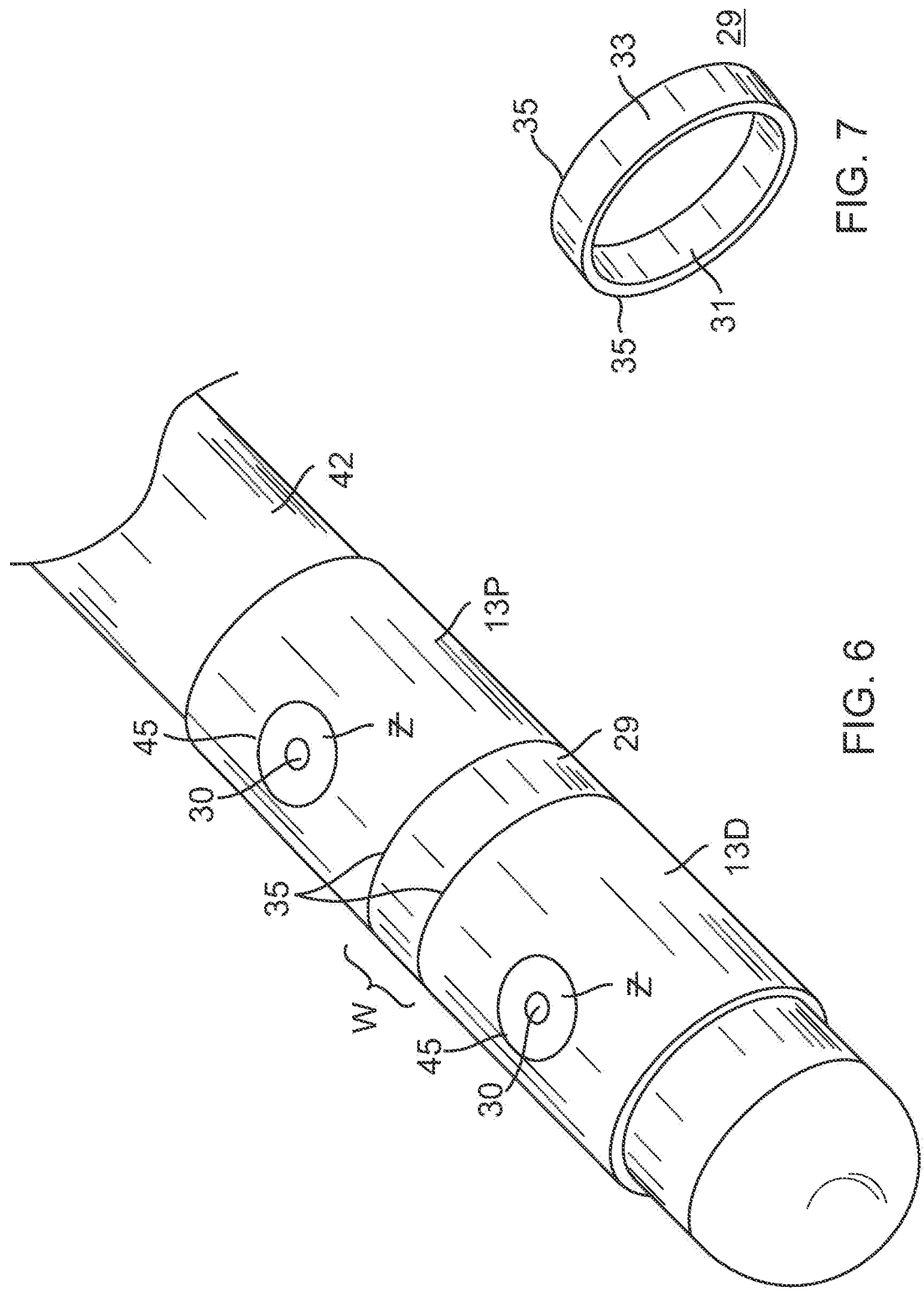
FIG. 6 is a detailed perspective view of a spine of the distal electrode assembly of FIG. 5.
FIG. 7 is a perspective view of a spacer of the present invention, in accordance with an embodiment.

With reference to FIG. 5 and FIG. 6, a plurality of bipole electrode pairs 13 are carried on each spine. Within each pair of bipole electrodes, a distal electrode 13D and a proximal electrode 13P are spaced apart and separated from each other by a predetermined distance by a spacer member 29 positioned therebetween. The spacer member 29 is constructed of a biocompatible, electrically-nonconductive material, for example, TEFLON or PEEK, and is sandwiched directly between the electrode pair, with edge-to-edge abutment and contact with the electrodes 13D and 13P to provide a physical and an electrical barrier between these adjacent proximal electrodes 13 of a pair. The predetermined separation gap provided by the spacer member 29 between adjacent electrodes 13P and 13D of a bipole pair is less than about 1.0 mm, preferably less than about 0.50 mm (500 microns), and more preferably about 0.05 mm (50 microns).

Figure 8:
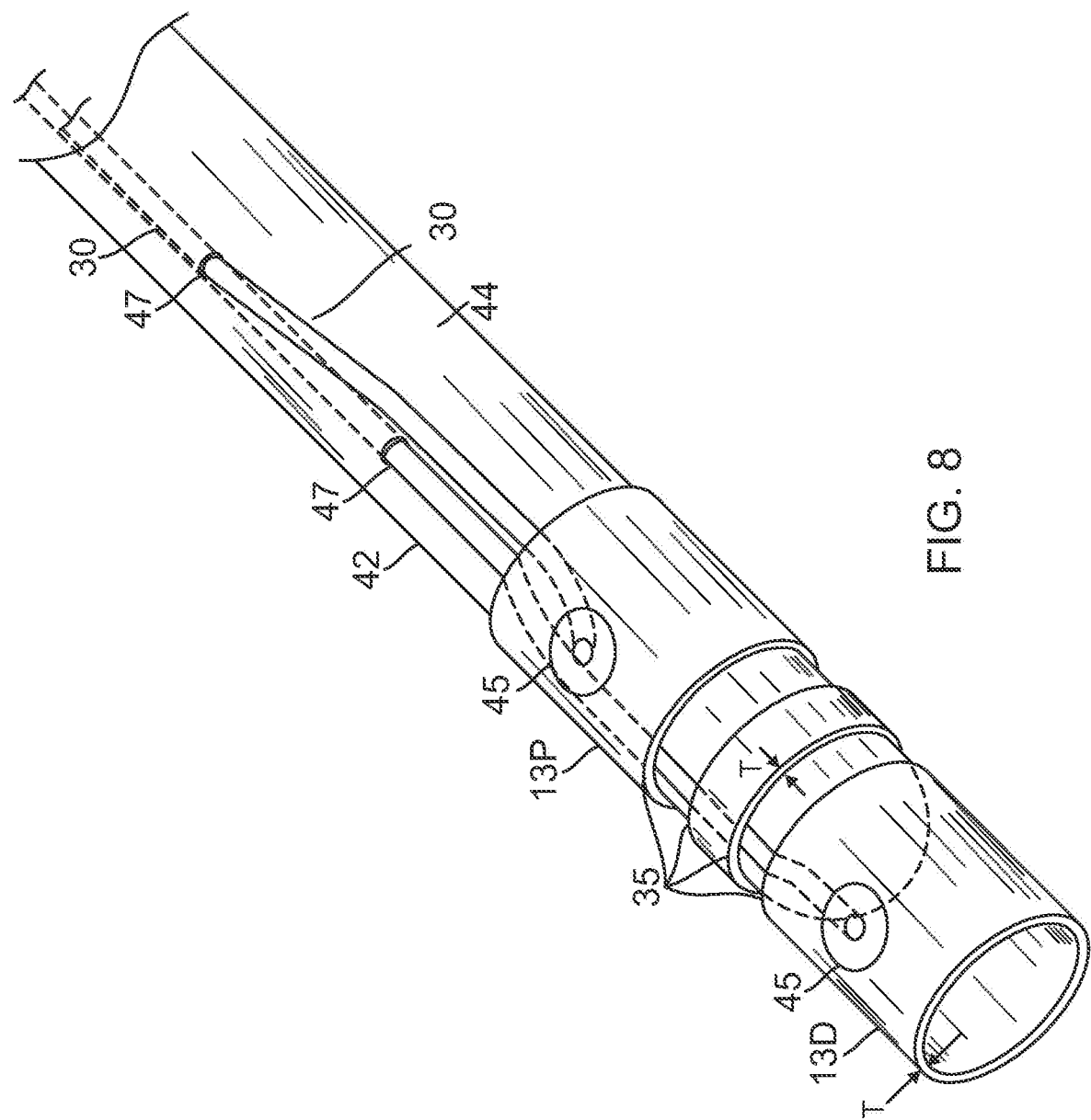
FIG. 8 is a perspective view of the spine of FIG. 6, during assembly.

With reference to FIG. 7 and FIG. 8, the spacer member 29 is hollow with an inner diameter that is slightly greater than the outer diameter of the spine 42 so that the spacer member can slide onto the spine. In some embodiments, the spacer member 29 has the same radial thickness T between its inner surface 31 and outer surface 33 as that of the distal and proximal ring electrodes 13D and 13P, and the spacer member 29 has complementary or mating adjacent edges 35 with those of the abutting ring electrodes 13D and 13P, so that the spacer member 29 and the electrodes 13D and 13P provide a generally seamless surface and profile on the catheter (see FIG. 6). In the illustrated embodiments, the electrodes 13D and 13P and the spacer member 29 are shaped similarly, for example, each as a "ring" with a closed circular band configuration spanning 360 degrees circumferentially, and both with similar inner and outer diameters, the inner wherein the spacer member 29 having a width W provides a generally equal separation gap W between ring electrodes 13P and 13D in the axial or longitudinal direction. The inner diameters define axial through-holes through which a spine is inserted during assembly of the distal electrode assembly.

In the assembly of a spine 42, according to one embodiment, apertures 47 are formed in the nonconductive covering 44 at predetermined positions along the spine, spaced at a predetermined space gap from each other. Lead wires 30 are passed from within the spine 42 to exit through the respective apertures 47, whereupon distal ends of the lead wires are further inserted into respective ring electrodes 13P and 13D to exit through apertures 45 formed in the ring electrodes, as shown in FIG. 8. The distal ends of the lead wires are welded at Z, or otherwise affixed in the apertures 45, with mechanical integrity for a fluid tight seal, and trimmed to present a flush surface with the outer surface of the ring electrodes.

The distal end of the spine 42 is then inserted through the proximal ring electrode 13P, followed by the spacer member 29, and further followed by the distal ring electrode 13D, as shown in FIG. 8, and the lead wires are drawn proximally or otherwise adjusted, as needed, to fit back into the spine 42 without leaving any excess length of lead wires outside of the spine 42. The spacer member and the electrodes are affixed to the outer surface of the spine by a suitable adhesive.

The electrodes 13P and 13D and the spacer member 29 are positioned on the spine 42 so that adjacent edges 35 of these three components are firmly abutting against each other, and each aperture 45 is generally concentric with its respective aperture 47. With the spacer member 29 having a precisely-measured minimized width W, and the electrodes 13D and 13P abutting directly and immediately against the spacer member 29, the spacer member serves to accurately minimize, define, and physically set and maintain the separation gap distance between adjacent electrodes. The spacer member ensures consistency and repeatability while simplifying the assembly process by advantageously eliminating the painstaking work of measuring and affixing electrodes at precise locations or separation distances from each other, and traversing the limitations of the space that would otherwise be physically occupied by the adhesive, such as epoxy, used to mount and seal the electrodes. The spacer member also advantageously provides uniformity in the separation gap distance of each bipole electrode pair between which a spacer is positioned such that bipole electrode pairs of one or more spines each have the same separation gap distance. Time and labor for assembly are therefore greatly reduced and streamlined.

As mentioned, each electrode has an aperture 45 formed in its sidewall. Generally corresponding aperture 47 are formed in the nonconductive coverings 44 of the spines 42. Each aperture 45 in the electrode 13 is sized, shaped and configured to receive a distal end of a respective lead wire 30 that is passed through a respective aperture 47 from the lumen of the nonconductive covering 44. In that regard, the lead wire 30 is made of a biocompatible, electrically conductive material, for example, MP35N. The aperture 47 may be sized and shaped in close conformity to the size and shape of the lead wire 30.

Figure 11:
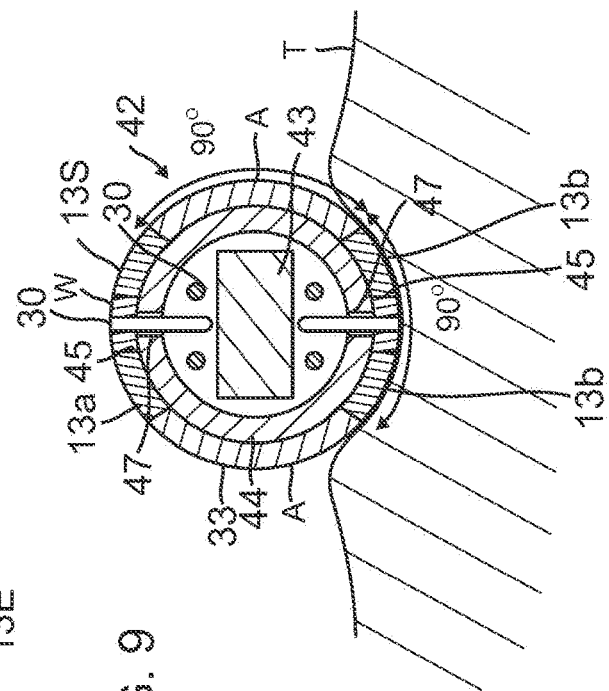
FIG. 11 is a cross-sectional view of the spine of FIG. 9 taken along line 11-11 in FIG. 9, in contact with tissue.
Figure 9:
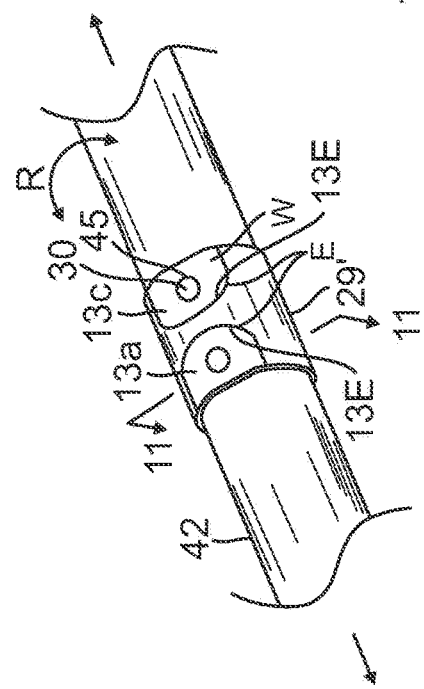
FIG. 9 is a detailed perspective view of a spine of a distal electrode assembly of the present invention, in accordance with another embodiment.
Figure 10:
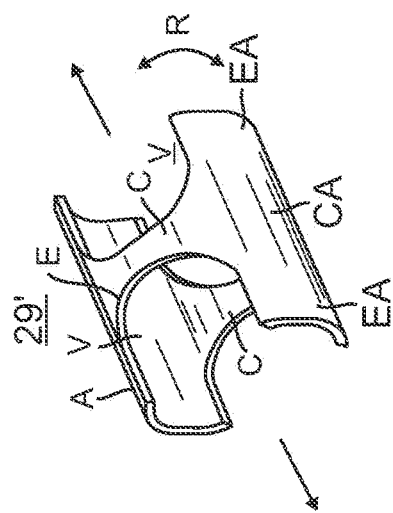
FIG. 10 is a detailed perspective view of a spacer of the present invention, in accordance with another embodiment.

In other embodiments, the electrodes 13 are "discrete," spanning less than 360 degrees circumferentially, as shown in FIG. 9, FIG. 10 and FIG. 11, wherein spacer member 29' provides separation gaps between adjacent electrodes in both the axial/longitudinal direction L and the circumferential direction C. In that regard, the spacer member 29' has a generally hollow cylindrical configuration, with an outer diameter, and an inner diameter that defines an axial through-hole through which a distal end of a spine is inserted during assembly of the distal electrode assembly. The spacer member 29' spans in the axial and circumferential directions, wherein the spacer member has axial extensions A, center portions CA of which are connected by circumferential extensions C, and end portions EA of which are separated by recessed voids V in the spacer member. Each void V in the spacer member 29' is occupied by a respective discrete electrode, and each discrete electrode is surrounded generally on three sides by two opposing axial extensions A and one circumferential extension C. Edges E defining the circumferential voids V and outer peripheral edges 13E of the electrodes 13 are complementary and provide a mating fit with each other so that the spacer member 29' and the electrodes 13 form a generally seamless surface and profile on the spine 42, as shown in FIG. 9. Outer surfaces 13S of the electrodes 13 and the outer surface 33 of the spacer member 29' together form a 360 degree circumferential surface that encircles and surrounds the outer surface of the spine 42. Notably, each circumferential void V has an open distal end or an open proximal end so that the electrodes 13 can advantageously slide in the axial direction (proximally or distally) into engagement with the spacer member 29 to occupy a respective void V.

In the illustrated embodiment of FIG. 9, FIG. 10 and FIG. 11, the spacer member 29' provides predetermined axial and circumferential separation gaps for four "discrete" electrode 13a, 13b, 13c, and 13d (13d not shown). The electrodes 13a and 13c are separated in the axial direction (and fixedly maintained in this separation configuration) by one circumferential extension C. The electrodes 13b and 13d are separated in the axial direction (and fixedly maintained in this separation configuration) by another circumferential extension C. The electrodes 13a and 13b are separated in the circumferential direction (and fixedly maintained in this separation configuration) by one circumferential extension A. The electrodes 13c and 13d are separated in the circumferential direction (and fixedly maintained in this separation configuration) by another circumferential extension A. The spacer member 29' is configured to receive distal electrodes 13a and 13b in a diametrically-opposed arrangement (on opposite sides of the spine), and proximal electrodes 13c and 13d in a diametrically-opposed arrangement (on opposite sides of the spine).

The spacer member 29' is also configured to position electrodes 13a and 13c in longitudinal alignment on the same side of the spine 42, and electrodes 13b and 13d in longitudinal alignment on the same and opposite side of the spine 42. The spacer member 29' is further configured so that each discrete electrodes spans about 90 degrees circumferentially, with each of the axial extensions A of the spacer member 29' spanning about 90 degrees between the electrodes 13a and 13b, and between the electrodes 13c and 13d (better seen in FIG. 11). With the electrodes in their discrete and divided configuration defined by the space member 29' on the spine 42, an operator may activate one or more selected electrodes for sensing and/or ablation with the remaining unselected electrodes being unactivated. For example, the spine 42 can be placed on target tissue surface T in a manner, as shown in FIG. 11, so that the operator selectively activates only the electrodes on the same side of the spine 42 that come into contact with the target tissue surface T, namely, electrodes 13b and 13d, for sensing electrical signals. Accordingly, electrodes on the opposite side of the spine 42 and not in contact with any tissue surface (namely, electrodes 13a and 13c in FIG. 11) may be selectively deactivated by the operator so as to avoid the detection of noise or far-field signals by these electrodes which may otherwise interfere with the signals detected by the electrodes 13b and 13d. In other embodiments, the signals received from selected electrode(s), for example, those not in contact with tissue, can be filtered out or otherwise processed and separated or distinguished from the signals received from selected electrode(s) in contact with tissue.

As for the signals detected by the electrodes on the same side of the spine (namely, electrodes 13b and 13d in FIG. 11), the width of the circumferential extension C advantageously provides a predetermined minimized space gap between these electrodes so that they may be used as a bipole electrode pair in the manner, as described above, to detect smaller/weaker signals.

It is understood that the configuration of spacer member 29' may be varied to receive additional electrodes greater than four. For example, the spacer 29' may receive eight electrodes with each distal electrode spanning about 45 degrees and each proximal electrode spanning about 45 degrees. Moreover, spacer members of different configurations may be used on a single spine as needed or appropriate. The shape of each discrete electrode of a spacer member can be any suitable shape, including circular, oval, square, rectangular, polygonal, etc.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter comprising:
   an elongated body;
   a distal section distal of the elongated body, the distal section including one or more spines, at least one of the one or more spines having at least first, second, third, and fourth electrodes mounted on an outer surface of the at least one spine, and a first nonconductive spacer member distinct from the at least one spine and mounted in a generally surrounding relationship on the outer surface of the at least one spine and configured to provide:
   a first axial separation gap between the first and third electrodes, the first and third electrodes configured as a first bipole electrode pair and being positioned in longitudinal alignment on a same first side of the at least one spine,
   a second axial separation gap between the second and fourth electrodes, the second and fourth electrodes configured as a second bipole electrode pair and being positioned in longitudinal alignment on a same second side of the at least one spine, a first circumferential separation gap between the first and second electrodes, and a second circumferential separation gap between the third and fourth electrodes.

2. The catheter of claim 1, wherein:

the first axial separation gap between the first and third electrodes is about 50 microns to about 200 microns; and/or the second axial separation gap between the second and fourth electrodes is about 50 microns to about 200 microns.

3. The catheter of claim 1, wherein:

the first axial separation gap between the first and third electrodes is smaller than 1.0 mm; and/or the second axial separation gap between the second and fourth electrodes is smaller than 1.0 mm.

4. The catheter of claim 1, wherein:

the first axial separation gap between the first and third electrodes is smaller than 0.5 mm; and/or the second axial separation gap between the second and fourth electrodes is smaller than 0.5 mm.

5. The catheter of claim 1, wherein:

the first axial separation gap between the first and third electrodes is about 0.05 mm;

and/or the second axial separation gap between the second and fourth electrodes is about 0.05 mm.

6. The catheter of claim 1, further comprising a respective lead wire connected to each of the first, second, third and fourth electrodes.

7. The catheter of claim 6, wherein each of the first, second, third and fourth electrodes has a respective electrode aperture in which its respective lead wire is anchored.

8. The catheter of claim 7, wherein the at least one spine comprises a nonconductive cover on which each of the first, second, third and fourth electrodes and the first spacer member are mounted.

9. The catheter of claim 8, wherein the nonconductive cover of the at least one spine comprises first, second, third and fourth spine apertures corresponding in location to the electrode apertures of the first, second, third and fourth electrodes, respectively.

10. The catheter of claim 9, wherein each respective lead wire is anchored in its respective one of the electrode apertures and enters the at least one spine through the respective one of the first, second, third or fourth spine apertures.

11. The catheter of claim 1, wherein the first spacer member comprises first and second circumferential extensions, and first and second axial extensions, wherein:

the first circumferential extension is configured to provide the first axial separation gap between the first and third electrodes, the second circumferential extension is configured to provide the second axial separation gap between the second and fourth electrodes, the first axial extension is configured to provide the first circumferential separation gap between the first and second electrodes, and the second axial extension is configured to provide the second circumferential separation gap between the third and fourth electrodes.

12. The catheter of claim 11, wherein the first axial extension spans about 90° between the first and second electrodes, and the second axial extension spans about 90° between the third and fourth electrodes.

13. The catheter of claim 1, wherein the first spacer member is configured such that the first and second electrodes are in a diametrically-opposed arrangement on the at least one spine, and such that the third and fourth electrodes are in a diametrically-opposed arrangement on the at least one spine.

14. The catheter of claim 1, the first and second sides of the at least one spine being generally opposite each other.

15. The catheter of claim 1, wherein each of the first, second, third and fourth electrodes spans about 90° circumferentially.

16. The catheter of claim 1, further comprising fifth, sixth, seventh and eighth electrodes, wherein:

the first axial separation gap comprises a first gap portion between the first electrode and the fifth electrode, and a second gap portion between the fifth electrode and the third electrode;

the second axial separation gap comprises a first gap portion between the second electrode and the seventh electrode, and a second gap portion between the seventh electrode and the fourth electrode; and the first spacer member further comprises:

a third circumferential separation gap between the fifth electrode and the seventh electrode, and a fourth circumferential separation gap between the sixth electrode and the eighth electrode.

17. The catheter of claim 16, wherein each of the first, second, third, fourth, fifth, sixth, seventh and eighth electrodes spans about 45° circumferentially.

18. The catheter of claim 16, wherein the first and second gap portions of the first axial extension each span about 45°, and the first and second gap portions of the second axial extension each span about 45°.

19. The catheter of claim 1, wherein the at least one of the one or more spines further comprises at least fifth and sixth electrodes and a second nonconductive spacer member mounted in a generally surrounding relationship on the at least one of the one or more spines at a longitudinal location different from a longitudinal location of the first spacer member, the second spacer member having at least a portion spanning between the fifth and sixth electrodes and configured to provide a separation gap between the fifth and sixth electrodes.

20. The catheter of claim 1, wherein the at least one of the one or more spines further comprises at least fifth, sixth, seventh and eighth electrodes, and a second nonconductive spacer member mounted in a generally surrounding relationship on the at least one of the one or more spines at a longitudinal location different from a longitudinal location of the first spacer member, the second spacer member configured to provide:

a third axial separation gap between the fifth and seventh electrodes, a fourth axial separation gap between the sixth and eighth electrodes, a third circumferential separation gap between the fifth and sixth electrodes, and a fourth circumferential separation gap between the seventh and eighth electrodes.

* * * * *